(12) United States Patent
Barford et al.

(10) Patent No.: US 7,230,714 B2
(45) Date of Patent: Jun. 12, 2007

(54) NONLINEAR FILTERING FOR EVENTS IN SPR SENSING

(75) Inventors: Lee A. Barford, San Jose, CA (US); Gregory D. VanWiggeren, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 384 days.

(21) Appl. No.: 10/971,604

(22) Filed: Oct. 22, 2004

(65) Prior Publication Data

US 2006/0087656 A1    Apr. 27, 2006

(51) Int. Cl.
  G01N 21/55    (2006.01)
(52) U.S. Cl. ..................................... 356/445
(58) Field of Classification Search .............. 356/445
  See application file for complete search history.

(56) References Cited

U.S. PATENT DOCUMENTS

2002/0063208 A1    5/2002    Hastings

FOREIGN PATENT DOCUMENTS

| EP | 0 969 283 A1 | 1/2000 |
|----|--------------|--------|
| WO | WO 03/081245 | 10/2003 |

OTHER PUBLICATIONS

Philippe Guedon, Thierry Livache, Francoise Martin, Frederic Lesbre, Andre Roget, Gerard Bidan, and Yves Levy—"Characterization And Optimization Of A Real-Time, Parallel, Label-Free, Polypyrrole-Based DNA Sensor By Surface Plasmon Resonance Imaging"; Analytical Chemistry, vol. 72, No. 24, Dec. 15, 2000; pp. 6003-6009.

Esa Stenberg, Bjorn Persson, Hakan Roos and Csaba Urbaniczky—"Quantitative Determination Of Surface Concentration Of Protein With Surface Plasmon Resonance Using Radiolabeled Proteins"; Journal Of Colloid And Interface Science, vol. 143, No. 2, May 1991; pp. 513-526.

U. Jonsson, L. Fagerstam, B. Ivarsson, B. Johnsson, R. Karlsson, K. Lundh, S. Lofas, B. Persson, H. Roos, I. Ronnberg, S. Sjolander, E. Stenberg, R. Tahlberg, C. Urbaniczky, H. Ostlin and M. Malmqvist—"Real-Time Biospecific Interaction Analysis Using Surface Plasmon Resonance And A Sensor Chip Technology"; BioTechniques, vol. 11, No. 5, 1991; pp. 620-622, 624-627.

Ronald L. Allen, Duncan W. Mills—"Signal Analysis—Time, Frequency, Scale and Structure"; IEEE Press, Wiley-Interscience; ISBN 0-471-23441-9; pp. 321-326.

C. L. Do Lago et al., "Applying Moving Median Digital Filter to Mass Spectrometry and Potentiomatric Titration", Analytica Chimica Acta, vol. 310, No. 2, Jun. 30, 1995, pp. 281-288.

*Primary Examiner*—Gregory J. Toatley, Jr.
*Assistant Examiner*—Amanda Merlino
(74) *Attorney, Agent, or Firm*—John L. Imperato

(57) ABSTRACT

A nonlinear filtering system determines the duration of a designated event in an SPR sensorgram, selects a filter length based on the determined duration of the designated event in the SPR sensorgram, and applies a nonlinear filter, having the selected filter length to the SPR sensorgram, to establish an output signal.

20 Claims, 4 Drawing Sheets

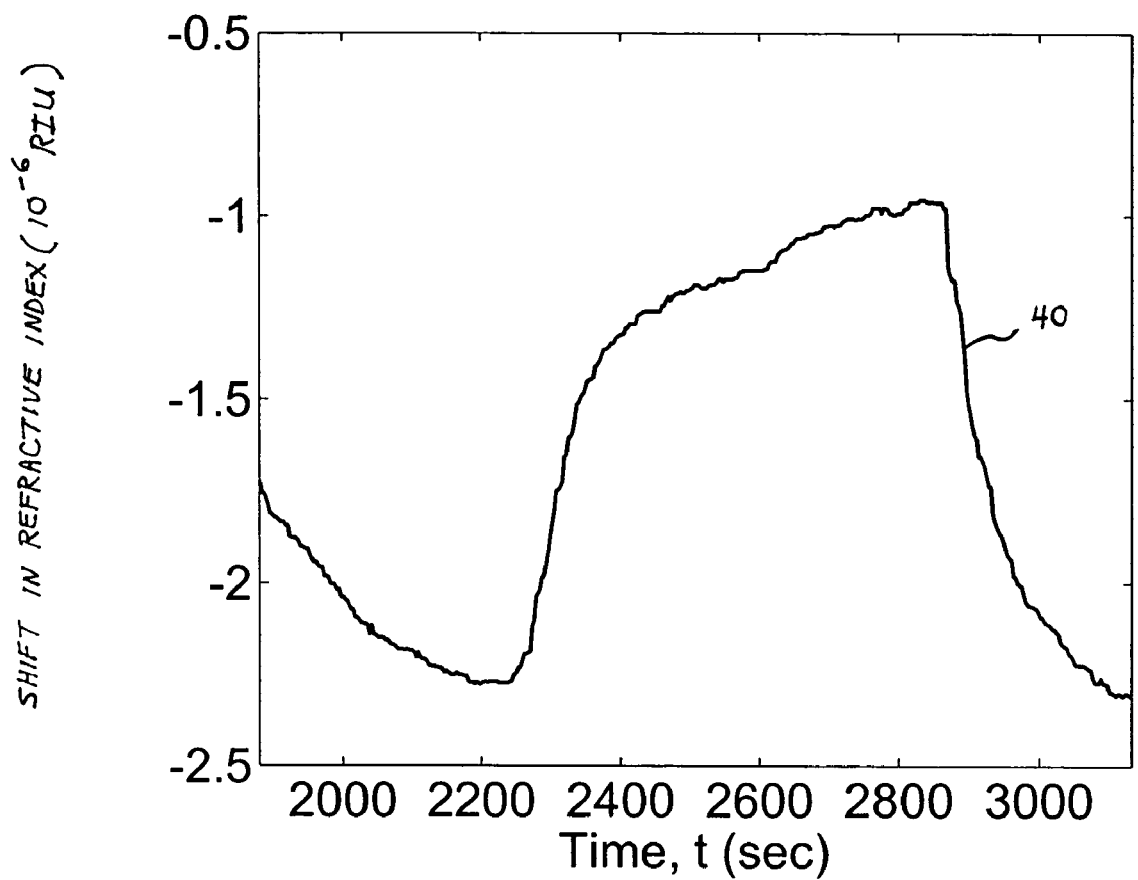
*Figure* 4

NONLINEAR FILTERING FOR EVENTS IN SPR SENSING

BACKGROUND OF THE INVENTION

Surface plasmon resonance (SPR) measurement systems rely on surface plasmon resonances to detect changes in refractive index of a sample, or target, proximate to a transducing interface. Due to the surface plasmon resonance phenomenon, optical signals that are incident on, and deflected at, the transducing interface undergo a loss at a resonant incidence angle and a resonant optical wavelength. Changes in the refractive index of the sample cause changes in the resonant incidence angle and the resonant optical wavelength. An SPR measurement system relates detected changes in the resonant incidence angle or resonant optical wavelength to corresponding changes in the refractive index of the sample, typically in the form of an SPR sensorgram, which is a plot of the relative refractive index of the sample versus time.

While SPR sensorgrams can be used to characterize biochemical processes within the samples based on relationships between the biochemical processes and refractive indices of the samples, the SPR sensorgrams include noise components that can mask or otherwise distort features of the SPR sensorgrams. Typically, the noise components are attributed to uncertainty in the measurement of relative refractive index of the samples by the SPR measurement system, or to mechanical events in the SPR measurement system, such as the opening or closing of valves that control the flow of buffer and analytes in the samples.

Linear filtering is commonly used in signal processing to reduce noise components that are present on a signal. However, when linear filtering, such as lowpass filtering, is applied to an SPR sensorgram, high frequency features, such as sharp transitions in the SPR sensorgram are smoothed out, or eliminated. However, the sharp transitions may be indicative of a critical biochemical process or event, such as the onset of a binding event between analytes and ligands within the sample. Smoothing out or eliminating the sharp transitions in the SPR sensorgram may make it difficult to determine association/dissociation rates and other important indicators of biochemical processes. Linear filtering can also result in ringing when a signal includes outlying data points, discontinuities, or other anomalies, making biochemical processes or events depicted in the SPR sensorgram difficult to interpret. Filters based on Fourier Transforms, FIR (finite impulse response) filters, IIR (infinite impulse response) filters, and numerous other classes of linear filters may not be well-suited for reducing noise components in SPR sensorgrams due to the signal features of the SPR sensorgrams and the resulting shortcomings of the linear filters when applied to the SPR sensorgrams.

SUMMARY OF THE INVENTION

A nonlinear filtering system according to embodiments of the present invention determines the duration of a designated event in an SPR sensorgram, selects a filter length based on the determined duration of the designated event in the SPR sensorgram, and applies a nonlinear filter, having the selected filter length, to the SPR sensorgram to establish an output signal.

BRIEF DESCRIPTION OF THE DRAWINGS

FIG. 4 shows the SPR sensorgram of FIG. 2 as modified by the nonlinear filtering system according to the embodiments of the present invention.

DETAILED DESCRIPTION OF THE EMBODIMENTS

Figure 1:
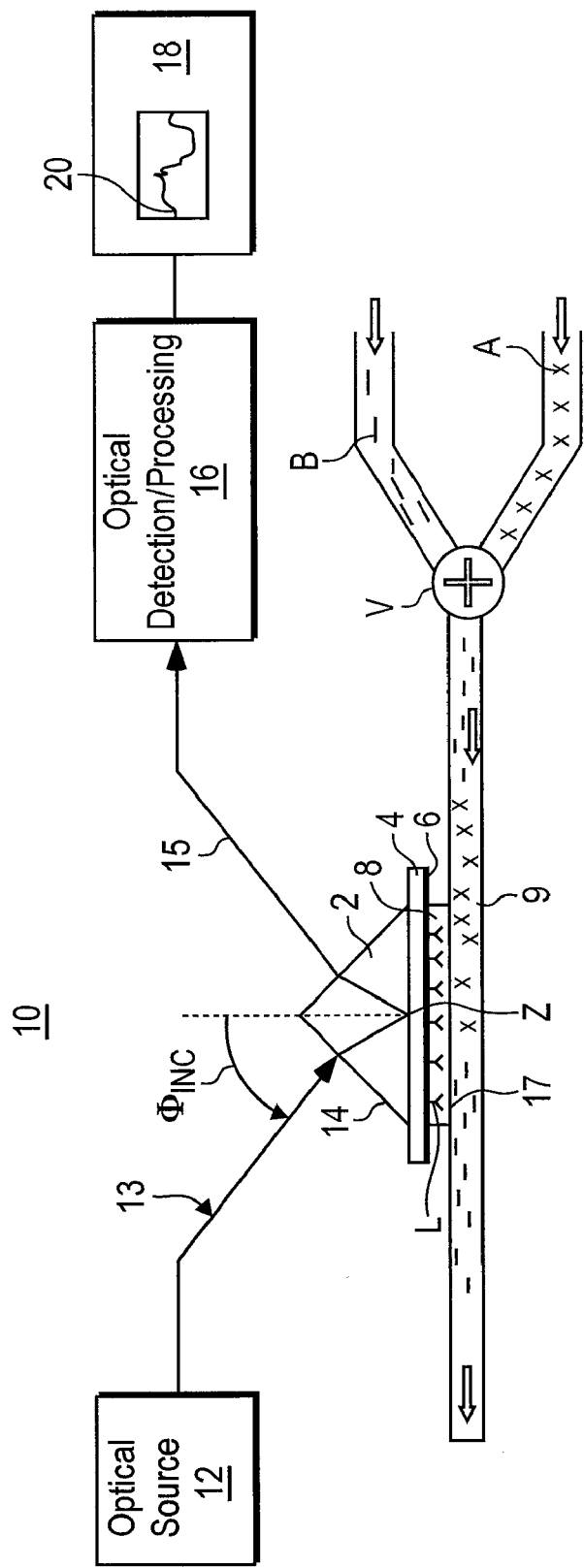
FIG. 1 shows a conventional SPR measurement system suitable for providing SPR sensorgrams.

FIG. 1 shows a conventional SPR measurement system 10. The SPR measurement system 10 includes an optical source 12 that provides optical stimuli 13 to an SPR transducer 14 and an optical detection/processing unit 16 that intercepts optical signals 15 that are reflected from the SPR transducer 14. Based on detection and processing of the reflected optical signals 15, the optical detection/processing unit 16 provides an SPR sensorgram 20 at an output device 18. The SPR measurement system 10 typically establishes SPR sensorgrams 20 using angle-based SPR wherein the optical source 12 provides optical stimuli 13 at various angles of incidence $\Phi_{INC}$ relative to the SPR transducer 14, or the SPR sensorgrams 20 are established using wavelength-based SPR wherein the optical source 12 provides optical stimuli 13 to the SPR transducer 14 that include multiple optical wavelengths.

The SPR transducers 14 included in the SPR measurement system 10 are well know in the art and can be constructed in a variety of ways. Typically, the SPR transducer 14 includes a prism 2, a glass slide 4 with a thin optically reflective backing 6, such as a gold film, and a dielectric, such as binding layer 8 that includes ligands L. The thin optically reflective backing 6 and binding layer 8 form a transducing interface 17 in the SPR transducer 14. Buffer B and analytes A are alternatively flowed past the binding layer 8 in a channel 9, typically formed in an elastomeric membrane, such as a polydimethylsilicone membrane. The flow of the buffer B and the analytes A is controlled according to a valve V that is coupled to the channel 9. References such as *Real-time Biospecific Interaction Analysis Using Surface Plasmon Resonance and a Sensor Chip Technology*, by Johnsson et al. BioTechniques, Vol. 11, No. 5 (1991), pages 620–627, and *Quantitative Determination of Surface Concentration of Protein with Surface Plasmon Resonance Using Radiolabeled Proteins*, by Stenberg et al., Journal of Colloid and Interface Science, Vol. 143, No. 2, May 1991, pages 513–526 provide examples of SPR transducers 14 suitable for inclusion in the SPR measurement system 10, although a variety of types of SPR transducers 14 can be used in the SPR measurement system 10.

The positions of the transducing interface 17 wherein the optical stimuli 13 are incident are referred to as targets Z. When the optical stimuli 13 are incident on a single target Z in the SPR transducer 14, the SPR sensorgram 20 corresponds to the single target Z. When the optical stimuli 13 are incident on multiple targets Z in the SPR transducer 14, multiple SPR sensorgrams 20 can be provided by the SPR measurement system 10, wherein each SPR sensorgram 20 corresponds to a designated one of the multiple targets Z.

Figure 2:
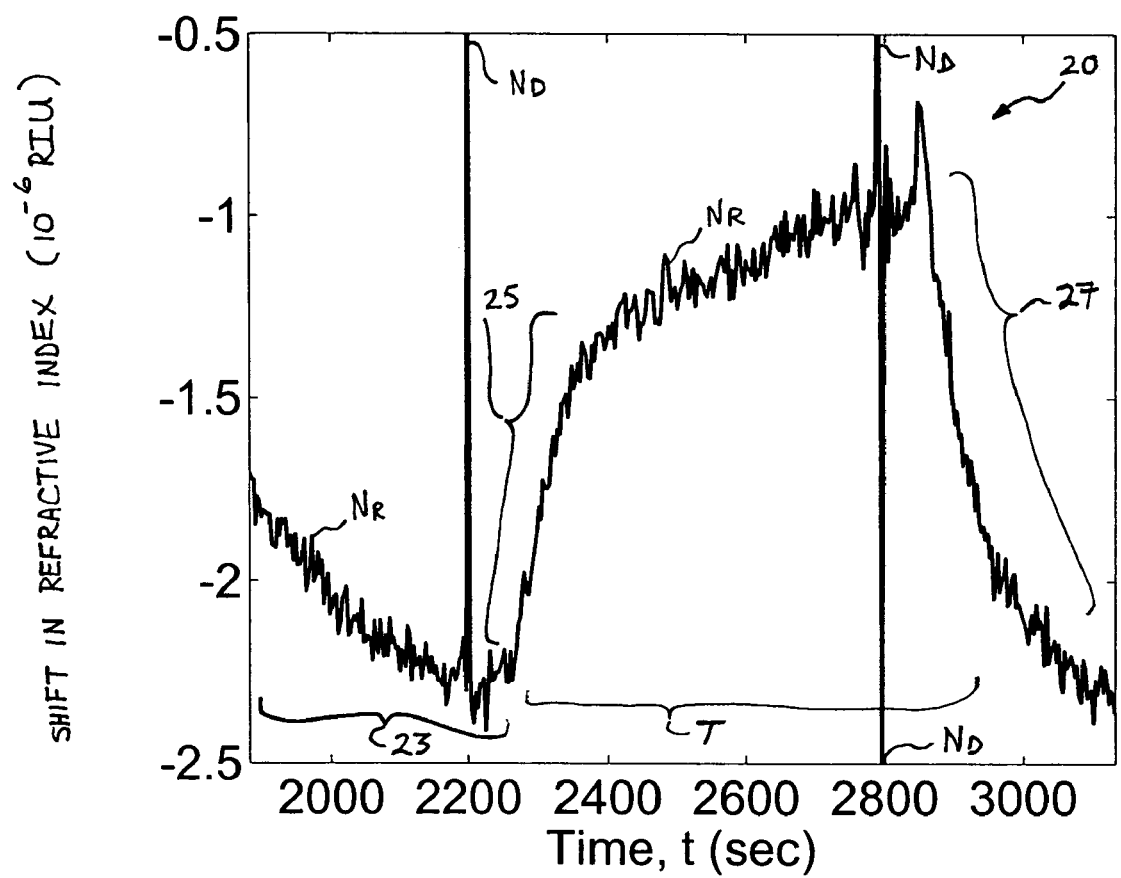
FIG. 2 shows one example of an SPR sensorgram associated with the SPR measurement system of FIG. 1.

FIG. 2 shows one example of an SPR sensorgram 20 provided by the SPR measurement system 10 shown in FIG.

1. The SPR sensorgram 20 represents the refractive index at the binding layer 8 of the transducing interface 17 versus time t. The refractive index is typically a relative refractive index, that indicates a shift or change in refractive index, depicted for example in micro-refractive index units ($10^{-6}$ RIU). A shift in refractive index represented in the SPR sensorgram 20 of FIG. 2 is typically derived from a correspondence to a shift in resonance angle of the SPR transducer or to a shift in resonant wavelength of the SPR transducer 14, depending on the type of SPR measurement system 10 used to provide the SPR sensorgram 20. While FIG. 2 shows one example of an SPR sensorgram 20, SPR sensorgrams 20 are well known in the art and are shown in references such as *Characterization and Optimization of a Real-Time, Parallel, Label-Free, Polypyrrole-Based DNA Sensor by Surface Plasmon Resonance Imaging*, by Guedon et al., Analytical Chemistry, Vol. 72, No. 24, Dec. 15, 2000, pages 6003–6009.

Features of the SPR sensorgrams 20 depict various physical or biochemical events that occur at the transducing interface 17 of the SPR transducer 14. For example, a first portion 23 of the SPR sensorgram 20 shown in FIG. 2 represents a time during which buffer B is flowing in the channel 9 past the transducing interface 17. During the time that corresponds to the first portion 23 of the SPR sensorgram 20, there is typically negligible interaction at the transducing interface 17 of the SPR transducer 14. A rising edge 25 on the SPR sensorgram 20 represents a biochemical event wherein analytes A flow in the channel 9 past the transducing interface 17 and bind to the ligands L at the transducing interface 17. The slope or steepness of the rising edge 25 of the SPR sensorgram 20 indicates the binding rates between the ligands L and the analytes A at the transducing interface 17. A trailing edge 27 of the SPR sensorgram 20 indicates dissociation of the analytes A and the ligands L. Thus, for a given concentration of analytes A and ligands L, the rising edge 25 and falling edge 27 of the SPR sensorgram 20 depict the binding kinetics at the transducing interface 17, and can provide association/dissociation constants at the transducing interface 17 of the SPR transducer 14. An event interval T between the rising edge 25 and the falling edge 27 of the SPR sensorgram 20 corresponds to a gating interval during which the valve V is set to a flow position that directs analytes A to the channel 9. The event interval T is offset in time from the gating interval by a delay that is based on the flow rate of the buffer B and the analytes A through the channel 9, and the distance between the valve V and the transducing interface 17.

FIG. 2 also indicates the various noise components that are present on the SPR sensorgram 20. One noise component is statistical or random noise $N_R$. This random noise $N_R$ is related to uncertainty in the measurements of refractive indices at the transducing interface 17 and produces the jitter that is present on the SPR sensorgram 20. Outlying data points $N_D$ are another noise component on the SPR sensorgram 20. The outlying data points $N_D$ are typically one or more switching transients due to the opening or closing of the valve V. However, the outlying data points $N_D$ can be due to any other type of perturbations or disruptions in the SPR measurement system 10. The length or duration of the outlying data points $N_D$ is typically shorter than the event interval T, between the rising edge 25 and the falling edge 27 of the SPR sensorgram 20. This length or duration can be expressed in units of time t, or as a number of data points n. The number of data points n is related to the duration in time t of the events in the SPR sensorgram 20 according to the relationship $n=t*R_S$, where $R_S$ is the sampling rate or data acquisition rate of the SPR measurement system 10 used to provide the SPR sensorgram 20. The outlying data points $N_D$ in the SPR sensorgram 20 show up as narrow spikes that are typically less than several data points in length or duration. The random noise $N_R$ has constituents or components of various length or duration. The nonlinear filtering system 40 according to embodiments of the present invention provides filtering of the noise components $N_R$, $N_D$ on the SPR sensorgram 20 that are shorter in length or duration than the event interval T. Thus, the outlying data points $N_D$ and random noise $N_R$ that have shorter duration than the event interval T can be reduced, or eliminated from the SPR sensorgram 20 by application of the nonlinear filtering system 30 to the SPR sensorgram 20.

Figure 3:
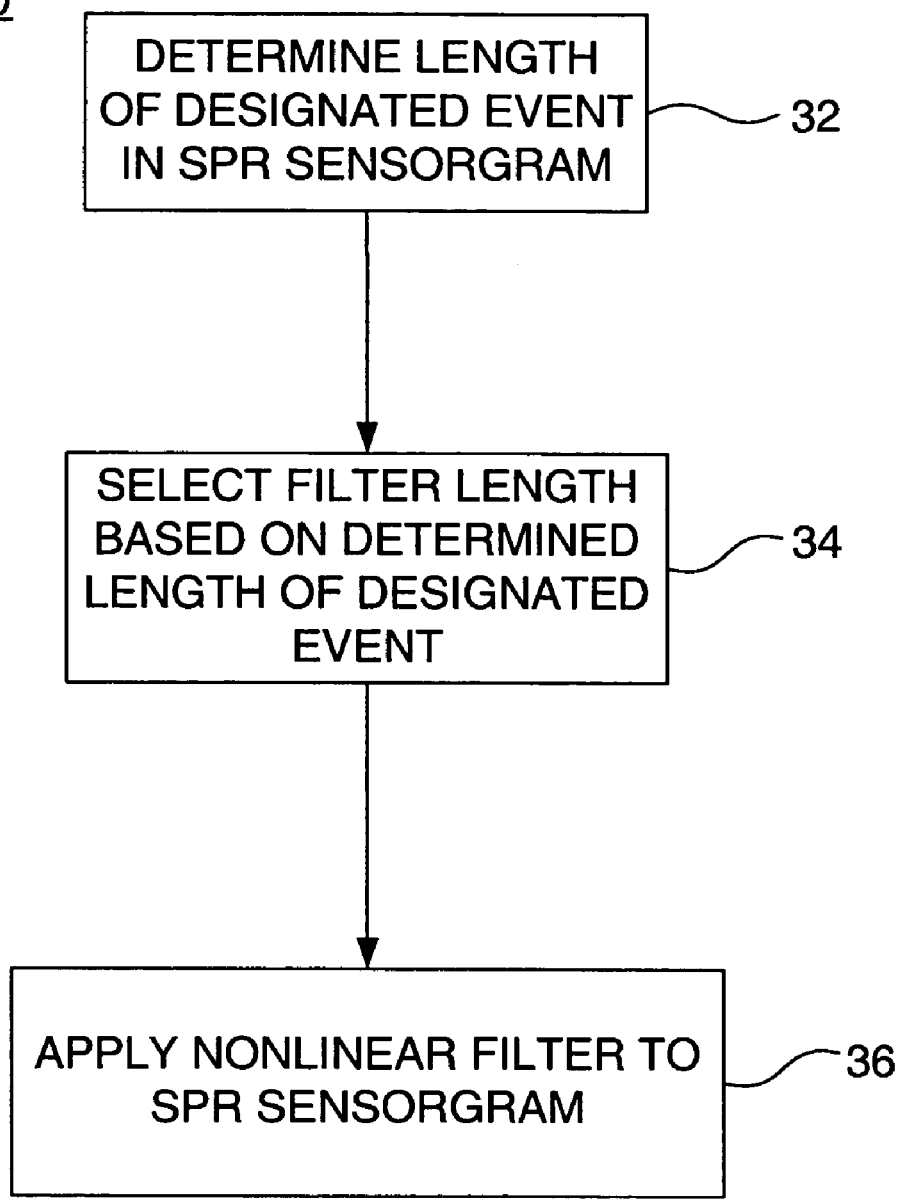
FIG. 3 shows a flow diagram of the nonlinear filtering system according to embodiments of the present invention.

FIG. 3 shows a flow diagram of the nonlinear filtering system 30. The nonlinear filtering system 30 includes determining the duration of a designated event in an SPR sensorgram 20 (step 32), selecting a filter length F based on the determined duration of the designated event in the SPR sensorgram 20 (step 34), and applying a nonlinear filter having the selected filter length F to the SPR sensorgram 20 to establish an output signal 40 (step 36).

In one example, the designated event in the SPR sensorgram 20 occurs within the event interval T between the rising edge 25 and the falling edge 27 of the SPR sensorgram 20 shown in FIG. 2. The event interval T corresponds to the time duration within which ligands L and analytes A interact at the transducing interface 17 of the SPR transducer 14. The determined duration of the event interval T, in this example, is expressed as a number of data points $N_1$ according to the relationship $N_1=T*R_S$, where T is the event interval expressed in units of time and $R_S$ is the sampling rate or data acquisition rate of the SPR measurement system 10. In one example, the designated event interval T has a duration in time of approximately 600 seconds, and the sampling rate or data acquisition rate $R_S$ is approximately one sample per three seconds. This results in the duration $N_1$ of the event interval T being 200 data points. However, the event interval T of the designated event, or the designated event in the SPR sensorgram 20, can vary depending on the configuration of the SPR measurement system 10, the type of SPR transducer 14, the characteristics of the buffer B, the analytes A and the ligands L, the flow rate of the buffer B and analytes A in the channel 9, the configuration of the channel 9, the gating interval during which the valve V is set to a flow position that directs analytes A to the channel 9, or any of a variety of parameters or factors that influence the SPR sensorgram 20.

The filter length F in the nonlinear filtering system 30 is typically expressed in terms of a number of data points. Typically, the filter length F is selected to not exceed $2*N_1$, or twice the duration $N_1$ of the designated event, expressed as a number of data points. In the example where the duration $N_1$ of the event interval T is 200 data points, the filter length F is selected to be less than 401 data points. Generally, a longer filter length provides greater filtering of the SPR sensorgram 20 than a shorter filter length provides. However, selecting the filter length F to be greater than or equal to $2N_1+1$ would result in filtering that reduces or eliminates the event interval T of duration $N_1$ as well as the noise components $N_S$, $N_D$ of shorter length or duration. Accordingly, the filter length F is selected not to exceed twice the duration $N_1$ of the designated event, but longer than twice the length or duration of the outlying data points $N_D$. This selection of the filter length F provides for adequate filtering of the outlying data points $N_D$ of the SPR sensorgram 20 and also reduces or eliminates constituents or components of the random noise $N_R$ that are less than half the filter length F. When the nonlinear filtering system 30 is applied to the SPR sensorgram 20 of FIG. 2, the output signal 40 of FIG. 4 results. The output signal 40 is a processed SPR sensorgram resulting from application of the nonlinear filtering system 30 to the SPR sensorgram 20. In the output signal 40 sharp spikes from the outlying data points $N_D$ are eliminated and the amount of the random noise $N_R$ on the SPR sensorgram 20 is reduced. The filter length F can be adjusted within the selected range previously indicated, based on the length or duration of the outlying data points $N_D$, the constituents of the random noise $N_R$, and the duration of designated events within the SPR sensorgram 20.

In one example, applying the nonlinear filter having the selected filter length F to the SPR sensorgram 20 in step 36 of the nonlinear filtering system 30 includes applying a median filter to the SPR sensorgram 20. Applying a median filter of filter length F to the SPR sensorgram 20 that includes data points represented as a signal $X=\{x(0), x(1) \ldots x(S-1)\}$ acquired or sampled at times $t(0), t(1) \ldots t(S-1)$, results in the output signal 40, represented by the signal Y, where each value Y(i) in the signal Y is expressed as $Y(i)=\text{median }\{x(i-N), x(i-N+1), \ldots, x(i-1), x(i), x(i+1), \ldots x(i+N-1), x(i+N)\}$, where S is the number of data points in the SPR sensorgram 20, where i is the index of data points X(i) in the signal X and the index of the resulting values Y(i) in the signal Y, and where N is an integer that is less than the duration $N_1$. The values Y(i) of the signal Y are undefined for i<N and i>S−N. For these undefined values of the signal Y, the data points X(i) of the SPR sensorgram 20 can be left unchanged in the output signal 40, or the sample points of the SPR sensorgram 20 can be set to a constant in the output signal 40. Alternatively, smaller median filters, that is median filters with a filter length substantially less than the selected filter length F, can be applied within the undefined portions i<N or i>S−N of the signal Y.

The values Y(i) of the signal Y representing the output signal 40 can be obtained using comparisons, such as the "≦" operation, to order successive sets of data points within the SPR sensorgram 20. Once ordered, the median of the data points can be readily selected, enabling the values Y(i) to be obtained using a computer program, an FPGA (field programmable gate array), an ASIC (application-specific integrated circuit), or any other suitable signal processor. In one example application of the nonlinear filtering system 30, the values Y(i) of the signal Y are obtained using a running median filter, such as "median1" available in Matlab™, to provide the output signal 40.

In alternative embodiments of the nonlinear filtering system 30, applying the nonlinear filter to the SPR sensorgram 20 as in step 46 includes applying any of a variety of morphological filters to the data points X(i) within the SPR sensorgram 20 to provide the output signal 40. Morphological filters are known in the art and are described in references such as *Signal Analysis: Time, Frequency, Scale and Structure*, by Ronald L. Allen and Duncan W. Mills, IEEE Press, ISBN 0-471-23441-9, pages 321–326.

When a morphological filter is applied in step 36, the filter length F of the morphological filter is also established in step 34 based on the duration of the designated event that is determined in step 32. Applying the morphological filter includes selecting a discrete function, called a structuring element h(i), where the index i is in the range—$N \leq i \leq N$. The values of the structuring element h(i) are typically designated to be greater than zero to provide adequate nonlinear filtering of the SPR sensorgram 20. In one example, the structuring element h(i) is established according to the relationship h(i)=R, for $-N \leq i \leq N$, where R is the range of the values of the data points in the signal X that represents the SPR sensorgram 20, indicated as R=(maximum of the signal X—minimum of the signal X). In another example, the structuring element h(i) is triangular, established according to the relationship h(i)=R*(1−abs(i)/N) for $-N \leq i \leq N$. In another example, the structuring element h(i) is semicircular, established according to the relationship h(i)=R cos($\pi$*i/N) for $-N \leq i \leq N$.

Applying the morphological filter to the SPR sensorgram 20 also includes defining an ERODE procedure ERODE(s, h) and a DILATE procedure DILATE(s,h) for a designated signal s(i), with $0 \leq i \leq P$, and the structuring element h(i), with $-N \leq i \leq N$. The ERODE procedure and the DILATE procedure are typically implemented as functions, subroutines, procedures or methods in C, JAVA, Matlab™ or other suitable computer language or program.

For $N \leq i < P-N$, the output E of ERODE(s, h) is designated as $E(i)=\min\{s(i-N)-h(-N), s(i-N+1)-h(-N+1), \ldots, s(i)-h(0), \ldots, s(i+N-1)-h(N-1), s(i+N)-h(N)\}$. For $N \leq i < P-N$, the output D of DILATE(s,h) is designated as $D(i)=\max\{s(i-N)+h(-N), s(i-N+1)+h(-N+1), \ldots, s(i)+h(0), \ldots, s(i+N-1)+h(N-1), s(i+N)+h(N)\}$. For $0 \leq i \leq N$ or $P-N \leq i \leq P$, the output D of DILATE(s,h) and the output E of ERODE(s, h) are undefined.

An OPEN procedure OPEN(s,h) and a CLOSE procedure CLOSE(s,h) are also defined in the application of the morphological filter to the SPR sensorgram 20 in step 46. The OPEN procedure and the CLOSE procedure are typically implemented as functions, subroutines, procedures or methods in C, JAVA, MATLAB or other suitable computer language or program. To compute O, the output of the OPEN procedure OPEN(s,h), the output E of ERODE(s, h) and the output D of DILAT(E,h) are computed. Then, the output D is assigned to O, the output of the OPEN procedure OPEN (s,h). To compute C, the output of the CLOSE procedure CLOSE(s,h), and the output O of the OPEN procedure OPEN(-s,-h) are computed. Then, C, the output of the CLOSE procedure CLOSE(s,h) is set to the output—O.

To establish M, the output of the morphologically filtered signal MORPH(s,h) obtained by applying structuring element h(i) to signal s(i), the output O of the OPEN procedure OPEN(s,h) and the output C of the CLOSE procedure CLOSE(O,h) are computed. Then M, the output of the morphologically filtered signal MORPH(s,h), is set to the output C, thus establishing M.

Applying the morphological filtering to the signal X that represents the SPR sensorgram 20 to produce the output signal 40, includes establishing M, the output of the morphologically filtered signal MORPH(X,h). Then, the signal Y is set to M.

Due to the output D of DILATE(s,h) and the output E of ERODE(s, h) being undefined for $0 \leq i \leq N$ or $P-N \leq i < P$, there are values Y(i) of the signal Y that are undefined. For these undefined values of the signal Y, the data points X(i) of the SPR sensorgram 20 can be left unchanged in the output signal 40, or the sample points of the SPR sensorgram 20 can be set to a constant in the output signal 40. Alternatively, smaller morphological filters, that is morphological filters with a filter length substantially less than the selected filter length F, can be applied within the undefined portions of the signal Y.

In other embodiments of the nonlinear filtering system 30, applying the nonlinear filter to the SPR sensorgram 20 includes applying any suitable function to the data points X(i) of the SPR sensorgram 20 that nonlinear filters the SPR sensorgram 20 according to the duration of events within the SPR sensorgram 20.

The nonlinear filtering system 30 according to the embodiments of the present invention provides an output signal 40 from an SPR sensorgram 20, wherein outlying data points $N_D$ and random noise $N_R$ are eliminated or substantially reduced. The output signal 40 is a processed SPR sensorgram that accurately indicates biochemical processes or conditions at the transducing interface 17 of the SPR transducer 14, enabling binding kinetics, even for ligands and analytes with weak interactions, to be accurately determined. The nonlinear filtering system 30 is readily implemented in software or hardware, or using a computer or other processor, either internal or external to the SPR measurement system 10. The nonlinear filtering system 30 can be stored on a computer readable medium.

While the embodiments of the present invention have been illustrated in detail, it should be apparent that modifications and adaptations to these embodiments may occur to one skilled in the art without departing from the scope of the present invention as set forth in the following claims.

The invention claimed is:

1. A nonlinear filtering system, comprising:
    determining a duration of a designated event in an SPR sensorgram;
    selecting a filter length based on the determined duration of the designated event in the SPR sensorgram; and
    applying a nonlinear filter having the selected filter length to the SPR sensorgram to establish an output signal.

2. The nonlinear filtering system of claim 1 wherein the filter length is selected to not exceed two times a duration of the designated event.

3. The nonlinear filtering system of claim 1 wherein the filter length is selected to be greater than two times the duration of one or more switching transients within the SPR sensorgram.

4. The nonlinear filtering system of claim 2 wherein the filter length is selected to be greater than two times the duration of one or more switching transients within the SPR sensorgram.

5. The nonlinear filtering system of claim 1 wherein applying a nonlinear filter having the selected length to the SPR sensorgram includes applying a median filter to the SPR sensorgram.

6. The nonlinear filtering system of claim 2 wherein applying a nonlinear filter having the selected length to the SPR sensorgram includes applying a median filter to the SPR sensorgram.

7. The nonlinear filtering system of claim 3 wherein applying a nonlinear filter having the selected length to the SPR sensorgram includes applying a median filter to the SPR sensorgram.

8. The nonlinear filtering system of claim 1 wherein applying a nonlinear filter having the selected length to the SPR sensorgram includes applying a morphological filter to the SPR sensorgram.

9. The nonlinear filtering system of claim 2 wherein applying a nonlinear filter having the selected length to the SPR sensorgram includes applying a morphological filter to the SPR sensorgram.

10. The nonlinear filtering system of claim 3 wherein applying a nonlinear filter having the selected length to the SPR sensorgram includes applying a morphological filter to the SPR sensorgram.

11. A nonlinear filtering system, comprising:
    a processor receiving an SPR sensorgram, determining a duration of a designated event in the SPR sensorgram, selecting a filter length based on the determined duration of the designated event in the SPR sensorgram, and applying a nonlinear filter having the selected length to the SPR sensorgram to establish an output signal.

12. The nonlinear filtering system of claim 11 wherein the filter length is selected to not exceed two times a duration of the designated event.

13. The nonlinear filtering system of claim 11 wherein the filter length is selected to be greater than two times a duration of one or more switching transients within the SPR sensorgram.

14. The nonlinear filtering system of claim 11 wherein applying a nonlinear filter having the selected length to the SPR sensorgram includes applying a median filter to the SPR sensorgram.

15. The nonlinear filtering system of claim 11 wherein applying a nonlinear filter having the selected length to the SPR sensorgram includes applying a morphological filter to the SPR sensorgram.

16. A computer readable medium that includes executable instructions for processing nonlinear filtering of an SPR sensorgram, the computer readable medium comprising;
    code for determining a duration of a designated event in the SPR sensorgram, selecting a filter length based on the determined duration of the designated event in the SPR sensorgram, and applying a nonlinear filter having the selected length to the SPR sensorgram to establish an output signal.

17. The computer readable medium of claim 16 wherein the filter length is selected to not exceed two times a duration of the designated event.

18. The computer readable medium of claim 16 wherein applying a nonlinear filter having the selected length to the SPR sensorgram includes applying a median filter to the SPR sensorgram.

19. The computer readable medium of claim 17 wherein applying a nonlinear filter having the selected length to the SPR sensorgram includes applying a median filter to the SPR sensorgram.

20. The computer readable medium of claim 16 wherein applying a nonlinear filter having the selected length to the SPR sensorgram includes applying a morphological filter to the SPR sensorgram.

* * * * *